United States Patent [19]

Disch et al.

[11] Patent Number: 5,223,166
[45] Date of Patent: * Jun. 29, 1993

[54] PREPARATIONS AND PROCESSES FOR CLEANING AND DISINFECTING ENDOSCOPES

[75] Inventors: Karlheinz Disch, Haan; Klaus Hachmann, Hilden; Klaus Bansemir, Langenfeld, all of Fed. Rep. of Germany

[73] Assignee: Henkel Kommanditgesellschaft auf Aktien, Duesseldorf-Holthausen, Fed. Rep. of Germany

[*] Notice: The portion of the term of this patent subsequent to Apr. 28, 2004 has been disclaimed.

[21] Appl. No.: 618,144

[22] Filed: Nov. 26, 1990

Related U.S. Application Data

[62] Division of Ser. No. 224,506, Jul. 26, 1988, Pat. No. 4,994,200, which is a division of Ser. No. 121,492, Nov. 17, 1987, Pat. No. 4,784,790.

[30] Foreign Application Priority Data

Nov. 17, 1986 [DE] Fed. Rep. of Germany ....... 3639322

[51] Int. Cl.$^5$ ................................................. C11D 3/48
[52] U.S. Cl. ..................................................... 252/106
[58] Field of Search ........................................... 252/106

[56] References Cited

U.S. PATENT DOCUMENTS

| | | | |
|---|---|---|---|
| 3,697,222 | 10/1972 | Sierra | 21/54 A |
| 3,886,204 | 5/1975 | Geffers et al. | 252/106 |
| 3,983,252 | 9/1976 | Buchalter | 424/333 |
| 4,469,614 | 9/1984 | Martin | 252/106 |
| 4,623,471 | 11/1986 | Wilsberg | 252/8.8 |
| 4,661,523 | 4/1987 | Disch et al. | 514/635 |
| 4,780,237 | 10/1988 | Schmid | 252/174.22 |
| 4,784,790 | 11/1988 | Disch et al. | 252/106 |
| 4,994,200 | 2/1991 | Disch et al. | 252/106 |

FOREIGN PATENT DOCUMENTS

| | | |
|---|---|---|
| 0028865 | 5/1981 | European Pat. Off. . |
| 0118933 | 9/1984 | European Pat. Off. . |
| 0158869 | 3/1985 | European Pat. Off. . |
| 0177183 | 4/1986 | European Pat. Off. . |
| 0224971 | 6/1987 | European Pat. Off. . |

*Primary Examiner*—John Niebling
*Assistant Examiner*—Brian M. Bolam
*Attorney, Agent, or Firm*—Ernest G. Szoke; Wayne C. Jaeschke; Henry E. Millson, Jr.

[57] ABSTRACT

In the cleaning and disinfection of endoscopes, the endoscope surfaces to be cleaned are successively a) brought into contact with a cleaning solution which is heated to 55° to 65° C., kept at that temperature for 1 to 15 minutes and then drained off and which contains a low-foam nonionic surfactant, a proteolytic enzyme, at least one complexing agent and, optionally, other standard detergent constituents, and has a pH value of from 6 to 8;

b) brought into contact with a disinfectant solution which is heated to 55° to 65° C., kept at that temperature for 1 to 15 minutes and then separated off and which contains an aldehyde selected from the group consisting of formaldehyde and aliphatic $C_2$–$C_8$ dialdehydes and at least one complexing agent, and has a pH value of from 6 to 8;

c) washed at least twice with water of which the pH value is adjusted to pH 6–8, the water being heated to 55° to 65° C. at least in the final wash cycle; and d) dried with sterilized hot air at 55° to 65° C., water having a hardness of from 3° to 8° Gh being used in steps a) to c).

10 Claims, No Drawings

PREPARATIONS AND PROCESSES FOR CLEANING AND DISINFECTING ENDOSCOPES

This application is a division of application Ser. No. 07/224,506, filed Jul. 26, 1988, now U.S. Pat. No. 4,994,200, which is a division of application Ser. No. 07/121,492, filed Nov. 17, 1987, now U.S. Pat. No. 4,784,790.

BACKGROUND OF THE INVENTION

1. Field of the Invention:

This invention relates to aqueous cleaning and disinfectant solutions, and to a process for cleaning and disinfecting endoscopes using such solutions.

2. Statement of Related Art:

In medical diagnosis and therapy, surgical operations are being replaced to an increasing extent by the use of endoscopes. This development has been made possible mainly by the fact that flexible glass fiber endoscopes have been available for some time. However, when used as directed, the endoscopes become massively infected with microorganisms which are present in body cavities, on the mucous membrane, and in the blood. Accordingly, used endoscopes have to be thoroughly cleaned and disinfected after each use.

Glass fiber endoscopes are extremely complicated precision instruments which have moving parts and which are made from a number of materials. They are extremely difficult to clean and disinfect for a number of reasons. Thus, not only the outer surfaces of the instrument, but also the narrow bores present in the interior have to be cleaned and disinfected. In view of the sensitivity of the materials involved, cleaning and disinfection have to be performed in such a way that no residues of the preparations used remain on the treated surfaces of the instrument. The extremely effective process of thermal sterilization normally used for medical instruments cannot be applied to endoscopes because endoscopes are made partly of temperature-sensitive materials. Another factor to be taken into consideration is that many of the metal parts present are susceptible to corrosion. Finally endoscopes should be able to be cleaned and disinfected in a short time so that they are always ready in good time for the treatment of the next patient. Only a few years ago were manufacturers of glass fiber endoscopes able to succeed in developing instruments which may be completely immersed in cleaning and disinfection baths and which are capable of withstanding temperatures of up to 70° C. without damage.

DESCRIPTION OF THE INVENTION

Other than in the operating examples, or where otherwise indicated, all numbers expressing quantities of ingredients or reaction conditions used herein are to be understood as modified in all instances by the term "about".

An object of the present invention is to develop a process which, through a combination of thermal and chemical treatments, enables endoscopes to be reliably cleaned and disinfected in a short time and which does not damage the treated instruments, even with long-term application. This process is also designed in such a way that it can be carried out, if desired, in an automatic washing machine. In addition, the process can be carried out in such a way that the spent cleaning and disinfecting solutions are sterile so that they may safely be added to normal wastewater. This object is achieved by the process described hereinafter.

While the process of the invention has particular application to endoscopes, the process can be used to clean and sterilize other surgical, medical, or dental devices and equipment, or in fact any equipment or devices having hard surfaces for any use where cleaning and disinfecting such hard surfaces is desired, particularly equipment and devices that cannot tolerate high temperature cleaning and sterilization. For ease of expression, the process will be described hereinafter for use with endoscopes.

The present invention relates to a process for cleaning and disinfecting endoscopes using aqueous cleaning and disinfectant solutions wherein the endoscope surfaces to be treated are successively a) brought into contact with a cleaning solution which is heated to 55° to 65° C., kept at that temperature for 1 to 15 minutes and then drained off, and which contains
   at least one low-foam nonionic surfactant,
   at least one proteolytic enzyme,
   at least one complexing agent and
   optionally other standard detergent ingredients, and has a pH value of from 6 to 8;

b) brought into contact with a disinfectant solution which is heated to 55° to 65° C., kept at that temperature for 1 to 15 minutes and then drained off, and which contains
   at least one aldehyde selected from formaldehyde and aliphatic $C_2$–$C_8$ dialdehydes and
   at least one complexing agent, and has a pH value of from 6 to 8;

c) rinsed at least twice with water of which the pH is adjusted to between 6 and 8, the water being heated to 55° to 65° C. at least in the last wash cycle; and d) dried with sterilized hot air at 55° to 65° C.; water having a hardness of 3° to 8° Gh (German hardness) being used in steps a) to c).

In step a) the cleaning solution contains:
from 0.1 to 1.0 g/l low-foam surfactant,
from 0.03 to 0.3 AU/l proteolytic enzyme, and
from 0.03 to 0.3 g/l complexing agent (AU=Anson Units). Low-foam nonionic surfactants suitable for use in the cleaning solution of step a) are, preferably, alkylene oxide adducts of the type obtainable by addition of from 3 to 30 moles of ethylene oxide and/or propylene oxide with aliphatic polyols containing from 2 to 6 hydroxyl groups and from 2 to 12 carbon atoms and with fatty alcohols, fatty acids, fatty amines or alkyl phenols each containing from 8 to 18 carbon atoms (the terminal hydroxyl groups of these polyglycol ether derivatives can be etherified, esterified or acetalated). Particularly suitable are adducts of from 3 to 15 moles of ethylene oxide with saturated and unsaturated $C_8$–$C_{18}$ fatty alcohols, adducts of from 3 to 5 moles of ethylene oxide and from 3 to 6 moles of propylene oxide with saturated and unsaturated $C_8$–$C_{18}$ fatty alcohols (these mixed alkylene oxide adducts may be prepared both by random and by block polymerization) and also ether derivatives of the above-described fatty alcohol alkylene glycol ethers in which the terminal hydroxyl groups are etherified with a straight-chain or branched-chain saturated aliphatic $C_4$–$C_8$ alcohol. Preferred are polyethylene glycol ethers corresponding to the following formula:

$$R^1-O-(CH_2CH_2O)_n-R^2 \qquad (I)$$

in which $R^1$ is a straight-chain or branched-chain $C_8$–$C_{18}$ alkyl or alkenyl radical, $R^2$ is a straight-chain or branched-chain $C_4$–$C_8$ alkyl radical and n is a number of from 7 to 12, and especially polyethylene glycol ethers of formula I in which $R^1$ is a mixture of $C_{12}$–$C_{18}$ alkyl and/or alkenyl radicals emanating from a hardened or unhardened tallow fatty alcohol and $R^2$ is an n-butyl radical while n is 9 or 10.

Particularly suitable proteolytic enzymes for the cleaning solution of step a) are proteases obtained from bacterial strains. Suitable enzymes are, for example, the enzymes obtained from Bacillus subtilis, Bacillus licheniformis and Streptomyces griseus. Corresponding commercial preparations are present either in the form of solutions of the enzyme in a mixture of water and an organic solvent, for example 1,2-propanediol, or as solid granulates. These commercial forms generally contain water-soluble calcium salts as potentiating and stabilizing agents. Solid preparations may be adjusted to a given degree of activity by diluents, for example sodium sulfate, sodium chloride, alkali phosphate or alkali polyphosphate.

Complexing agents for use in the cleaning solution of step a) include, for example, alkali salts of nitrilotriacetic acid, ethylenediamine tetra-acetic acid, 1-hydroxyethane-1, 1-diphosphonic acid, amino-tris-(methylenephosphonic acid), ethylenediamine tetrakis-(methylenephosphonic acid), phosphonobutane tricarboxylic acid, tartaric acid, citric acid, and gluconic acid; sodium gluconate being particularly preferred.

The disinfectant solution of step b) preferably contains
from 0.5 to 5 g/l aldehyde and
from 0.02 to 0.25 g/l complexing agent.

Examples of the aliphatic $C_6$–$C_8$ dialdehydes that can be present in the disinfectant solution of step b) are glyoxal, malonaldehyde, succinaldehyde, and glutaraldehyde. The disinfectant solution used in step b) of the process of the invention preferably contains glutaraldehyde.

The disinfectant solution of step b) may contain as complexing agents the same compounds which were described above as constituents of the cleaning solution of step a). Sodium salts of phosponobutane tricarboxylic acid are preferably used in the disinfectant solution of step b).

Water having a hardness of from 3° to 8° Gh is used in the process of the invention. This applies both to the preparation of the cleaning and disinfectant solution and also to the wash cycles. The above degrees of hardness are best adjusted by passing tapwater at least partly over a cation exchanger which removes the cations responsible for hardness from the water. This cation exchange results in a displacement of the pH value into the alkaline range. For this reason, the pH value has to be adjusted to the indicated range of pH 6 to pH 8. The cleaning solution and the disinfectant solution are generally prepared from concentrates which will be described hereinafter. These concentrates may be formulated in such a way that they give solutions having a pH value in the required range on dilution with the tapwater treated with the cation exchanger. The water used for the wash cycles is adjusted to a pH value in the range from pH 6 to pH 8 with physiologically safe organic acids, for example with acetic acid, tartaric acid, lactic acid, malic acid, citric acid, etc.

The spent cleaning solutions from step a) are preferably disinfected before drainage into the wastewater system. To this end, a concentrated disinfectant solution based on formaldehyde or an aliphatic $C_2$–$C_8$ dialdehyde, and complexing agents can be added to the cleaning solutions before drainage in such a quantity that, after their addition, from 0.25 to 2.5 g/l of aldehyde and from 0.1 to 0.13 g/l of complexing agent are present in the solution as a whole.

If desired, a wash cycle can be interposed between step a) and step b), again being carried out with water adjusted to pH 6–8.

During their treatment with the cleaning and disinfectant solution in steps a) and b) of the process of the invention, the endoscopes can be simultaneously exposed to the effect of ultrasound to enhance the cleaning and disinfecting effect.

Air sterilized before heating by suction through a microfilter is preferably used to dry the endoscopes in step d).

The process of the invention can be carried out, for example, in closable, heatable fine-steel containers of appropriate dimensions which are provided with means for pumping the various liquids and the hot air used for drying through the endoscope bores to be cleaned. In addition, the containers contain inlets and outlets for the cleaning and disinfectant solution and for the washing water and also for the hot air used to dry the instruments. It is of advantage if the endoscopes to be treated can be placed in a rack which fits in the fine steel container. To carry out the individual steps of the process of the invention, the container is charged with such quantity of liquid that the endoscopes are fully immersed therein. The particular liquid present is continuously pumped at an adequate rate through the bores of the endoscope. When the treatment liquids are drained off, it is important to ensure that the liquid present in the bores is also removed.

Automatic washing machines of the type known and commonly used for the cleaning of laboratory instruments and medical instruments are particularly suitable for carrying out the process of the invention, providing they have the necessary attachments, for example means by which the liquids can be pumped through the bores of the endoscopes. The outer surfaces of the endoscopes are not brought into contact with the liquids by immersion therein, but instead by continuous spraying.

The cleaning and disinfectant solutions are generally prepared from stable, storable concentrates which, in addition to the active ingredients already described, contain further constituents of the type normally present in such concentrates.

An aqueous detergent concentrate for preparing the cleaning solution used in step a) may contain, for example,
from 5 to 10% by weight low-foam nonionic surfactant,
from 7.1 to 77 AU/l proteolytic enzyme,
from 1 to 5% by weight complexing agent,
from 10 to 50% by weight enzyme stabilizer,
from 1 to 5% by weight blending aid and
from 0.05 to 0.5% by weight preservative.

The pH value of the concentrate is adjusted to pH 4–6 with acid, base or an acid-base mixture.

Suitable enzyme stabilizers for the aqueous detergent concentrate are, for example, triethanolamine, morpholine, α-pyrrolidone, ethylene glycol, propylene glycol, glycerol, water-soluble calcium salts or mixtures of these compounds, Glycerol and/or propylene glycol is preferably used as the enzyme stabilizer.

Blending aids (solution promoters) suitable for the aqueous detergent concentrate are, for example, sodium cumene sulfonate, sodium toluene sulfonate, sodium xylene sulfonate, urea, polyethylene glycols, methyl acetamide and fatty alcohols, such as cetyl alcohol. Sodium cumene sulfonate is preferably used as the blending aid.

The above detergent cencentrates of the invention are susceptible to microbial infestation. Fungal growth is readily observed, particularly in the case of preservative-free compositions. For this reason, effective quantities of preservatives are added to the concentrates. Suitable preservatives are, for example, p-hydroxybenzoic acid methyl ester, 5-bromo-5-nitro-1,3-dioxane, glutaraldehyde, salicylic acid, O-2-naphthyl-m-N-dimethyl thiocarbanilate, 5-chloro-5-methyl-4-isothiazoline-3-one, 2-meth yl-4-isothizoline-3-one nd mixtures of the last two compounds. p-hydroxybenzoic acid methyl ester is preferably used as the preservative.

The observations in the foregoing description of the process of the invention apply fully to the constituents present in the aqueous detergent concentrate, namely the low-foam nonionic surfactant, the proteolytic enzyme and the complexing agent.

An aqueous disinfectant concentrate for preparing the disinfectant solution used in step b) may contain, for example, from 10 to 40% by weight of at least one aldehyde selected from formaldehyde and aliphatic $C_2$–$C_8$ dialdehydes, from 0.5 to 2% by weight of at least one complexing agent and from 7 to 15% by weight blending aid.

The pH value of the concentrate is adjusted to pH 3–5 with acid, base or an acid-base mixture.

Particularly suitable blending aids for the disinfectant concentrate are lower aliphatic alcohols, such as ethanol, n-propanol and isopropanol and also ethylene glycol and triacetin. Ethanol is preferably used as the blending aid.

The observations in the foregoing description of the process of the invention again apply fully to the constitutents present in the aqueous disinfectant concentrate, namely the aliphatic dialdehyde and the complexing agent.

The invention is illustrated but not limited by the following example.

EXAMPLE

Concentrates were prepared by mechanically blending the following individual constituents (pbw=parts by weight):

| Detergent concentrate | |
|---|---|
| 8 | pbw n-butyl ether of an adduct of 9.5 moles ethylene oxide with 1 mole hardened tallow fatty alcohol (formula I: $R^1$ = $C_{12}$–$C_{18}$ alkyl, $R^2$ = $C_4$ alkyl; n = 9.5) |
| 1 | pbw proteolytic enzyme (Alcalase ™, a product of Novo Industri A/S, Basvaerd, Denmark: 2.5 AU/g) |
| 6 | pbw glycerol |
| 3 | pbw 1,2-propylene glycol |
| 2.5 | pbw sodium gluconate |
| 2 | pbw citric acid |
| 3 | pbw sodium cumene sulfonate |

| Detergent concentrate -continued | |
|---|---|
| 0.1 | pbw p-hydroxybenzoic acid methyl ester |
| ad 100 | pbw water |

The mixture was adjusted to pH 5 with 37% by weight sodium hydroxide solution.

| Disinfectant concentrate | |
|---|---|
| 20 | pbw glutaraldehyde |
| 1 | pbw phosphonobutane tricarboxylic acid |
| 8 | pbw ethanol |
| ad 100 | pbw water |

The mixture was adjusted to pH 4 with 50% by weight sodium hydroxide solution.

The endoscopes were cleaned and disinfected in a closable, heatable fine-steel vessel (diameter approx. 60 cm; height approx. 65 cm) which was provided with inlets and outlets for the cleaning and disinfectant solution, for the water used in the wash cycles and for the hot air used to dry the instruments. The apparatus was provided with a circulation pump by which the particular liquid present could be pumped through the bores of the fiber endoscopes.

The tests were carried out with a standard commercial gastroscope.

Water adjusted by means of a cation exchanger to a hardness of 5°Gh was used to prepare the cleaning and disinfectant solution. The same water was used to carry out the wash cycles after it had been adjusted to pH 7 with lactic acid.

A cleaning solution containing 0.45 g/l surfactant, 0.06 g/l enzyme and 0.14 g/l sodium gluconate was prepared by dilution of the detergent concentrate. A disinfectant solution containing 2.4 g/l glutaraldehyde and 0.12 g/l phosphonobutane tricarboxylic acid was prepared by dilution of the disinfectant concentrate.

The air used for drying was drawn through a microfilter and, before introduction into the fine steel vessel, was passed through a heating zone in which it was heated to 60° C.

To carry out the cleaning process, the endoscope was placed in the fine-steel container in a wire basket. The bores of the endoscope were connected to the circulation pump. In the individual steps of the process, water was delivered to the fine-steel container in such a quantity that the endoscope was completely immersed. During the individual steps of the process, the liquid present was continuously pump-circulated through the bores of the endoscope.

After the fine-steel vessel had been filled with cleaning solution, the cleaning solution was heated to 60° C. and kept at that temperature for 10 minutes. The cleaning solution was then drained off and replaced by the disinfectant solution which was again heated to 60° C. and kept at that temperature for 10 minutes. After the disinfectant solution had been separated off, the endoscope was washed twice with cold water. The fine-steel vessel was then refilled with water which was heated to 60° C. and then drained off. Finally, sterile hot air was introduced for 5 minutes to dry the endoscope.

In a modification of the process, disinfectant concentrate was added to the cleaning solution of step a) before drainage in such a quantity that the solution as a whole contained 1.2 g/l glutaraldehyde and 0.06 g/l phosphonobutane tricarboxylic acid.

To test the disinfecting effect obtained in the process of the invention, the bores of the endoscope were contaminated with a microorganism suspension which, in a first series of tests, contained a mixture of the following microorganisms:

1) approx. $10^8$ microorganisms/ml *Staphylococcus aureus*
2) approx. $10^8$ microorganisms/ml *Escherichia coli*
3) approx. $10^8$ microorganisms/ml *Pseudomonas aeruginosa*
4) approx. $10^8$ microorganisms/ml *Proteus mirabilis*
5) approx. $10^8$ microorganisms/ml *Candida albicans*

In a second series of tests, the microorganism dispersion contained only 6) approx. $10^8$ microorganisms/ml *Streptococcus faecalis*.

To simulate practical conditions, the microorganism suspensions contained an addition of 20% by weight defibrinated sheep's blood.

For contamination, the bores of the endoscope were filled with the microorganism suspension. After brief standing, the microorganism suspensions were drained off again. 1 hour after contamination, the endoscope was cleaned and disinfected in accordance with the invention. 0.5 l of a solution containing 3% by weight Tween 80, 0.3% by weight lecithin, 0.1% by weight histidine, 0.1% by weight tryptone and 0.05% by weight sodium chloride was then drawn through the bores of the endoscope. 1 ml samples of this solution were inoculated onto agar plates which were then incubated for at least 48 hours at 37° C. or for at least 72 hours at 35° C. and subsequently tested for any microorganism growth present.

It was found that, where the process of the invention was applied, the necessary freedom from microorganisms was obtained in every instance.

We claim:

1. An aqueous disinfectant concentrate consisting essentially of from about 10 to about 40% by weight of at least one aldehyde selected from the group consisting of formaldehyde, glyoxal, malonaldehyde, succinaldehyde, and glutaraldehyde; from about 0.5 to about 2% by weight of at least one complexing agent selected from the group consisting of an alkali metal salt of nitrilotriacetic acid, ethylenediamine tetra-acetic acid, 1-hydroxyethane1,1-diphosphonic acid, aminotris-(methylenephosphonic acid), ethylenediamine tetrakis-(methylenephosphonic acid), and phosphonobutane tricarboxylic acid; and from about 7 to about 15% by weight of at least one blending aid selected from the group consisting of a lower aliphatic alcohol, ethylene glycol, and triacetin, wherein the pH of the concentrate is in the range of 3-5.

2. The concentrate of claim 1 wherein the blending aid is one or more of ethanol, n-propanol, isopropanol, ethylene glycol, or triacetin.

3. The concentrate of claim 2 wherein ethanol is the blending aid.

4. The concentrate of claim 1 wherein the blending aid is at least one lower aliphatic alcohol.

5. The concentrate of claim 1 which is diluted with water and which contains from about 0.5 to about 5 g/l of aldehyde and from about 0.02 to about 0.25 g/l of complexing agent.

6. An aqueous disinfectant concentrate consisting essentially of from about 10 to about 40% by weight of at least one aldehyde selected from the group consisting of formaldehyde and aliphatic $C_2$-$C_8$ dialdehydes, from about 0.5 to about 2% by weight of the alkali metal salt of phosphonobutane tricarboxylic acid, and from about 7 to about 15% by weight of at least one blending aid selected from the group consisting of a lower aliphatic alcohol, ethylene glycol, and triacetin, wherein the pH of the concentrate is in the range of 3-5.

7. The concentrate of claim 6 which contains glutaraldehyde as the aliphatic dialdehyde.

8. The concentrate of claim 6 wherein the dialdehyde is glyoxal, malonaldehyde, succinaldehyde, or glutaraldehyde.

9. An aqueous disinfectant concentrate comprising:
   from about 10 to about 40% by weight of glutaraldehyde,
   from about 0.5 to about 2% by weight of an alkali metal salt of phosphonobutane tricarboxylic acid, and
   from about 7 to about 15% by weight of ethanol,
   wherein the pH of the concentrate is in the range of pH 3-5.

10. The concentrate of claim 9 which is diluted with water and which contains from about 0.5 to about 5 g/l of aldehyde and from about 0.02 to about 0.25 g/l of complexing agent.

* * * * *